United States Patent [19]

Darsow

[11] Patent Number: 5,162,517
[45] Date of Patent: Nov. 10, 1992

[54] PROCESS FOR THE PREPARATION OF EPIMER-FREE SUGAR ALCOHOLS FROM THE GROUP CONSISTING OF XYLITOL, SORBITOL (D-GLUCITOL), 4-O-β-D-GALACTOPYRANOSYL-D-GLUCITOL AND 4-O-α-D-GLUCOPYRANOSYL-D-SORBITOL

[75] Inventor: Gerhard Darsow, Krefeld, Fed. Rep. of Germany

[73] Assignee: Bayer Aktiengesellschaft, Leverkusen, Fed. Rep. of Germany

[21] Appl. No.: 585,747

[22] Filed: Sep. 20, 1990

[30] Foreign Application Priority Data

Oct. 14, 1989 [DE] Fed. Rep. of Germany ....... 3934457
Oct. 14, 1989 [DE] Fed. Rep. of Germany ....... 3934458
Nov. 25, 1989 [DE] Fed. Rep. of Germany ....... 3939058
Jan. 13, 1990 [DE] Fed. Rep. of Germany ....... 4000839

[51] Int. Cl.⁵ ............... C07H 1/00; C08B 37/00; C07C 27/00; C07C 29/00
[52] U.S. Cl. .................... 536/124; 536/125; 536/4.1; 568/861; 568/862; 568/863
[58] Field of Search .............. 568/861, 862, 863; 536/124, 125, 4.1

[56] References Cited

U.S. PATENT DOCUMENTS

| | | | |
|---|---|---|---|
| 3,784,408 | 1/1974 | Jaffe et al. | 568/863 |
| 4,029,878 | 6/1977 | Kruse | 536/125 |
| 4,322,569 | 3/1982 | Chao et al. | 568/863 |
| 4,684,720 | 8/1987 | Darsow et al. | 536/124 |

FOREIGN PATENT DOCUMENTS 0152779 8/1985 European Pat. Off.

Primary Examiner—Ronald W. Griffin
Assistant Examiner—Everett White
Attorney, Agent, or Firm—Sprung Horn Kramer & Woods

[57] ABSTRACT

The sugar alcohols given in the title can be prepared in epimer-free form from the corresponding sugars by catalytic hydrogenation in aqueous solution using hydrogen, the hydrogenation being carried out continuously at 100–500 bar of $H_2$ and 60°–125° C. on a fixed bed of carrier-free mouldings composed of pressed powders of the elements of the iron group of the periodic table. The mouldings have a compressive strength of above 50 N and an internal surface of 10–90 $m^2/g$.

13 Claims, No Drawings

PROCESS FOR THE PREPARATION OF EPIMER-FREE SUGAR ALCOHOLS FROM THE GROUP CONSISTING OF XYLITOL, SORBITOL (D-GLUCITOL), 4-O-β-D-GALACTOPYRANOSYL-D-GLUCITOL AND 4-O-α-D-GLUCOPYRANOSYL-D-SORBITOL

BACKGROUND OF THE INVENTION

1. Field of the Invention

The invention relates to a process for the preparation of the sugar alcohols mentioned above in the title, in epimer-free form, from the corresponding sugars xylose, α-D-glucose, 4-O-β-D-galactopyranosyl-α-D-sorbitol or 4O-α-D-glucopyranosyl-α-D-glucopyranose by continuous catalytic hydrogenation using hydrogen. The course of the reaction can be illustrated by means of the following reaction schemes:

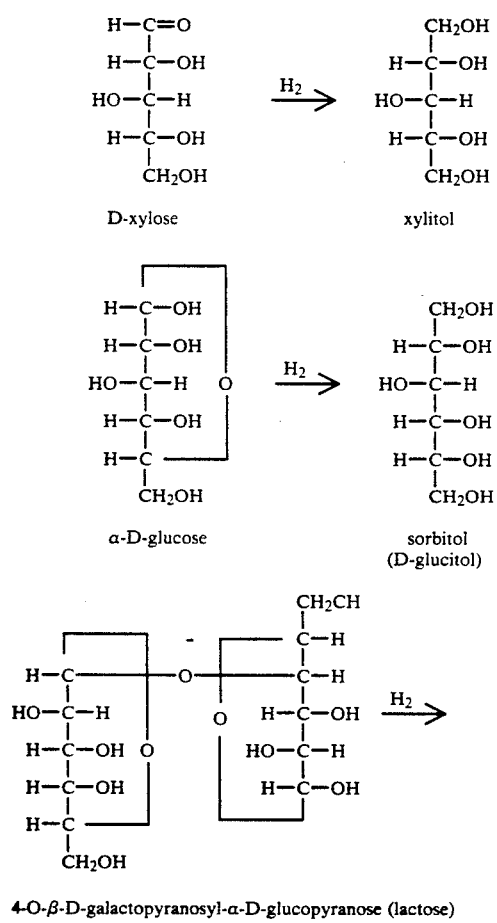

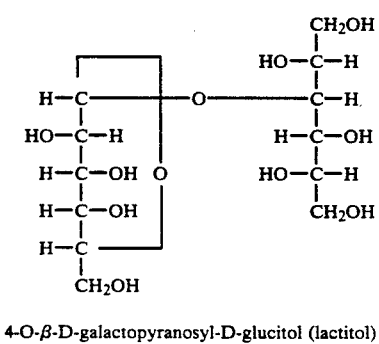

4-O-β-D-galactopyranosyl-D-glucitol (lactitol)

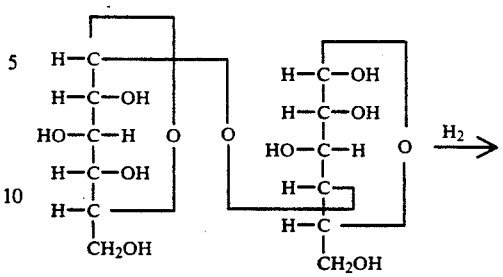

4-O-α-D-glucopyranosyl-α-D-glucopyranose (maltose)

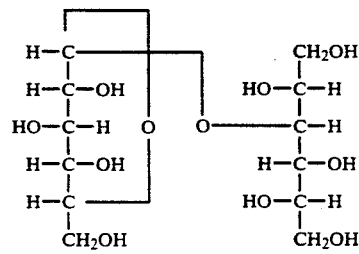

4-O-α-D-glucopyranosyl-D-sorbitol (maltitol)

The four sugar alcohols which can be prepared in eipmer-free form according to the invention are known and can be described as follows:

The sweetening potency of xylitol reaches about 80–100% of the sweetening potency of sucrose. The potency can be increased by adding to the aqueous solution artificial sweeteners, for example cyclohexyl sulphamate or methyl phenylalanine-aspartate, and the product can be obtained in crystalline form by joint vacuum crystallization. However, it is also possible to mix the artifical sweeteners in solid form with the crystallized xylitol. Xylitol can also be mixed in liquid or solid form with other sweet-tasting carbohydrates, for example maltitol, lactitol, sorbitol and the like.

Owing to its pleasantly sweet taste, xylitol is suitable as a sugar replacement in diabetic diets and as a non-cariogenic sweetener in confectionery and oral pharmaceuticals. The use of xylitol in diabetic food is permitted in unlimited amounts in accordance with the dietary statute (Federal German Law Gazette I 1982, page 71).

Pure xylitol is particularly well suited for processing in confectionery such as sweets and chewing gum (Swiss Dent. I (7/8) 1980, page 25 to 27). Even products for treating the mouth and pharyngeal cavities such as toothpastes, sore throat tablets, and cough sweets are increasingly sweetened with xylitol (Swiss Dent. III (7/8) 1982, page 25 to 30).

In the human body, sorbitol is only resorbed to a minor extent and only this proportion is broken down. Sorbitol is therefore suitable as a sugar substitute for diabetics and as a low-calorie sweetener. Furthermore, it is less cariogenic than glucose or other sugars.

The potency of sorbitol reaches about 50–60% of the potency of sucrose. The potency can be increased by adding to the aqueous solution artificial sweeteners, for example cyclohexyl sulphamate or methyl phenylalanineaspartate and the product can be obtained in crystalline form by joint vacuum crystallization. However, it is also possible to mix the artificial sweeteners in solid form with the crystallized sorbitol. Sorbitol can also be mixed in liquid or solid form with other sweet-tasting carbohydrates, for example maltitol, lactitol, xylitol and the like.

So far it has not been possible to identify any toxic effects, even in long term studies (Ullmanns Encyklopädie der technischen Chemie, Volume 24, Weinheim 1983, p. 774), and therefore there are many suitable applications in the food sector in the preparation of diabetic products and of sugar-free sweets and foods having a low nutritive value.

Xylitol or sorbitol is often prepared by a discontinuous process (batch process) in which a pulverulent nickel catalyst is employed in suspension.

In the human body, lactitol is not broken down as a carbohydrate and in the small intestine is neither hydrolyzed nor absorbed. Lactitol is therefore suitable as a sugar substitute for diabetics. Moreover, it is less cariogenic than sucrose.

The potency of lactitol reaches about 40% of the potency of sucrose. The potency can be increased by adding to the aqueous solution artificial sweeteners, for example cyclohexyl sulphamate or methyl phenylalanineaspartate and the product can be obtained in crystalline form by joint vacuum crystallization. However, it is also possible to mix the artificial sweeteners in solid form with the crystallized lactitol. Lactitol can also be mixed in liquid or solid form with other sweet-tasting carbohydrates, for example fructose, sorbitol, xylitol and the like.

So far it has not been possible to detect any toxic effects, even in long term studies (Ullmanns Encyklopädie der technischen Chemie, Volume 24, Weinheim 1983, p. 779), and therefore there are many suitable applications in the food sector in the preparation of diabetic products and of sugar-free sweets and foods having a low nutritive value.

In the human body, maltitol is broken down only with difficulty by amylolytic enzymes. Maltitol is therefore suitable as a sugar substitute for a calorie-reduced diet and for diabetics (Ullmann's Encyklopädie der technischen Chemie, Volume 24, Weinheim 1983, p. 771).

The potency of maltitol reaches the potency of sucrose. Maltitol can be mixed in liquid form with other sweet-tasting carbohydrates, for example fructose, sorbitol, xylitol and the like. The use of maltitol in the beverage industry is particularly advantageous owing to its high potency and very low tendency to crystallize even at high concentrations.

2. Description of the Realted Art

EP 39,981 discloses a discontinuous process (batch process) for the preparation of lactitol, which has so far not been detected in nature, this process employing a pulverulent nickel catalyst in suspension.

U.S. Pat. No. 3,741,776 discloses a discontinuous process (batch process) for the preparation of maltitol, which has so far not been detected in nature, this process employing a pulverulent nickel catalyst in suspension.

Discontinuous processes have the disadvantage that their capacity is very small in relation to the reaction volume, and therefore large reaction apparatuses and storage tanks are necessary. The energy consumption is uneconomical and the manpower requirements are relatively high.

Part of the abovementioned disadvantages are avoided in continuous powder-catalyzed processes which function using a plurality of cascaded hydrogenation reactors. However, the troublesome manner of selectively activating, circulating and quantitatively filtering off the pulverulent catalyst from the reaction product still remains. The catalyst slurry pumps are subjected to high mechanical stress. The quantitative removal of the pulverulent catalyst is expensive (alternate arrangements of coarse and fine filtration apparatuses). Furthermore, there is a high risk that the catalyst will lose its activity relatively quickly owing to the additional operations (high catalyst consumption). It is therefore desirable that the reaction proceeds over fixed-bed catalysts which must have a high specific activity which must also be sustained for a relatively long period of 1 to several years since frequent catalyst exchange is also expensive in the case of fixed bed reactions.

It is also customary with fixed bed catalysts to connect several reactors in succession, this giving a plurality of reaction zones connected in series (DE-A-3,214,432).

Use is made of nickel catalysts on a carrier ($SiO_2$/$Al_2O_3$), these catalysts having extremely high active surfaces of 140–180 $m^2$/g so that the catalysts are so active that they must be stabilized by additional chemical treatment methods, for example by oxygen gas absorption to form monomolecular oxygen layers on the catalyst surface (DE-A-3,110,493). However, the deactivating stabilization of the catalyst then requires such high reaction temperatures during the hydrogenation of sugars (130–180° C.) that uncontrollable side reactions can occur such as discoloration by caramelization and destructive hydrogenation (hydrogenolysis) of the saccharide alcohols to the extent that methanol and even methane are produced. Moreover, with this type of reaction, heavy metals such as nickel, iron or cobalt continuously go into solution in ionic or colloidal form which necessitates on the one hand a subsequent treatment of the hydrogenated product with activated carbon and on the other hand deionization using ion exchangers.

Since the known hydrogenation processes operate on sugar solutions having a pH which has been adjusted to 7–13, basic alkali metal compounds or alkaline earth metal compounds must be added to the starting solutions and must likewise be removed from the end product with difficulty (DE-A-3,110,493; DE-A-3,214,432).

Moreover, it is expected that, under the hydrogenation conditions, significant epimerization will occur, so that, for example, D-xylose gives not only xylitol but also lyxitol (arabinitol and ribitol); $\alpha$-D-glucose is expected to give not only sorbitol but also mannitol.

Furthermore, the splitting effect on the carbohydrate chain of sugars during catalytic hydrogenation on Raney nickel is known; DE-A-2,756,270 describes this effect on a sugar mixture such as is obtained from the auto-condensation of formaldehyde, a significant shift from longer carbon chain lengths to shorter carbon chain lengths being observed within the scope of the cited exemplary embodiments. According to DE-A-2,831,659, this type of splitting is not observed on precious metal catalysts of sub-group 8.

EP 152,779 discloses a process for the hydrogenation of $\alpha$-D-glucopyranosido-1,6-fructose on fixed bed catalysts. However, in this process a mixture of two reduction products is obtained, in particular $\alpha$-D-glucopyranosido-1,6-mannitol and $\alpha$-D-glucopyranosido-1,6sorbitol in a ratio of about 1:1.

It was therefore surprising that in the present invention the sugars are not only virtually completely converted but, with the avoidance of epimerization and carbon chain splitting and also with the avoidance of the formation of higher molecular weight components by condensation reactions with ether formation, only one sugar alcohol, as described earlier in the reaction schemes, is obtained. This is of importance for the direct use of the product as a diet component without further purification.

SUMMARY OF THE INVENTION

A process for the preparation of epimer-free sugar alcohols from the group consisting of xylitol, sorbitol (D-glucitol), 4-O-β-D-galactopyranosyl-D-glucitol (lactitol) and 4-O-α-D-glucopyranosyl-D-sorbitol (maltitol) by catalytic hydrogenation of the corresponding sugars D-xylose, α-D-glucose, 4-O-β-D-galactopyranosyl-α-D-glucopyranose or 4-O-D-glucopyranosyl-α-D-glucopyranose in aqueous solution using hydrogen under elevated pressure and at elevated temperature, has been found, characterized in that the hydrogenation is carried out continuously at a hydrogen pressure of 100-500 bar and temperatures of 60°-125° C. in a reaction zone by the fixed bed process over hydrogenation catalysts in the form of carrier-free mouldings having a compressive strength of more than 50 N, preferably 100-400 N, onto the surface of the mouldings, and an internal surface of 10 to 90 m$^2$/g, these mouldings being made from one or more elements of the iron group of the periodic table.

DETAILED DESCRIPTION OF THE INVENTION

Within the scope of the present invention, epimer-free means having an epimer content which is negligible insofar as the purity of the abovementioned sugar alcohols allows these sugar alcohols to comply with the commercial specifications as given in the German Pharmacopoeia (DAB) and in the United States Pharmacopoeia (USP) and in the Food Chemicals Codex (FCC), without further purification steps.

In the process according to the invention, the sugar alcohols are obtained in virtually quantitative yield. This is of particular importance, since the elimination of harmful impurities of higher molecular weight (caused by ether formation) or lower molecular weight (caused by hydrogenolysis) from the reaction product by additional purification processes such as recrystallization from solvents usually requires considerable environmental expenditure for the disposal of these impurities. The sugar alcohols of the lyxitol type (arabitinol and ribitol) which are epimers of xylitol are detectable in the reaction product in at most trace amounts (total<0.3%). The diastereoisomer of sorbitol, mannitol, is present in the reaction product in at most trace amounts (<0.3%). The diastereoisomer of lactitol, 4-O-β-D-galactopyranosyl-D-mannitol and the diastereoisomer of maltitol, 4-O-α-D-glucopyranosyl-D-mannitol, are not detectable in the reaction product in each case.

In contrast to catalysts containing carriers, the fixed bed catalysts which are to be used according to the invention have no tendency to "bleed", i.e. to transfer catalyst components in ionic or colloidal form into the solution phase of the substrate, and therefore the substrate is not contaminated by heavy metals which can likewise usually only be removed from the substrate with difficulty, for example using ion exchangers, at environmental cost. After depletion, the catalysts which are to be used can readily be worked up, since the heavy metals do not need to be separated with difficulty from a carrier. Furthermore, with polyhydroxyl compounds there was the perceived tendency to form complex chelate compounds with heavy metal ions, the complexes being separable from solutions only with difficulty.

Accordingly, it is possible in the process according to the invention to prepare the particular sugar alcohol in the dry state with a purity of above 99%. The proportion of unconverted sugar reaches values only of 0.2% or below. Since the glycosidic ether linkages in disaccharides remain intact, the proportions of the mono-sugar alcohols are only 0.3% or below. The commercial specifications for the sugar alcohols, for example those according to DAB, USP or FCC, can normally be complied with directly without further purification steps.

The starting compound used for the process according to the invention is pure crystalline D-xylose or pure α-D-glucose or pure α-lactose or α-lactose monohydrate or pure maltose (liquid or, in its β-form, also as the crystalline monohydrate). The starting material is dissolved in oxygen-free deionized water to give a 15-45% by weight strength, preferably 35-40% by weight strength, solution whose pH is 3.5-10.5. Monosaccharide solutions are preferably adjusted to a pH of 3.5-8, and disaccharide solutions are preferably adjusted to a pH of 5.5-10.5. The particularly preferred pH range for all starting materials is 6-7.5. The sugars which have been designated as starting compounds, when dissolved in water of pH 7, give a neutral solution or, owing to the formation of traces of sugar acids, a weakly acidic solution, but this solution can be adjusted to the desired pH in a manner known to a person skilled in the art, for example by adding sorbic acid or citric acid.

The hydrogenation according to the invention employs pure hydrogen, which is pre-compressed to a pressure of 100-500 bar, preferably 150-300 bar. The hydrogenation is carried out continuously by the fixed bed process on catalysts which are described in more detail below, by passing the solution which is to be hydrogenated either in co-current flow in the upwards direction together with the previously admixed hydrogen over the catalyst which has been mounted in a hydrogenation reactor (co-current process) or else by bringing the upward-flowing solution which is to be hydrogenated into contact with the stream of hydrogen which is introduced from above (counter-current process).

The hydrogenation reactor may either be a single high pressure tube made from steel or from a steel alloy and which is fully or partly filled with the catalyst, the use of catalysts on trays (wire baskets or similar) also being advantageous at certain tube cross-sections, or else it may be a jacketed bank of high pressure tubes whose individual tubes are completely or partly filled with catalyst. Furthermore, instead of a relatively large single tube reactor, it is possible to use an assembly of a plurality of small single tube reactors in succession in a cascade.

The carrier-free catalysts are processed from metal powders of the elements of the iron group of the periodic table, in particular nickel, cobalt or mixtures thereof or alloys with one another or with iron, particularly preferably from nickel or from mixtures containing at least 70% of nickel, to give mouldings. For this purpose, powders of the individual metals or pulverized alloys of the abovementioned metals can be employed. The mouldings are prepared by conventional methods in which the metal powder is pressed, for example on pelleting machines under high pressure, it being possible to improve the adhesion of the metal particles by also using graphite and/or adhesives in amounts of 0.5-3% by weight, relative to the total weight of the components forming the catalyst. The mouldings are prepared in an oxygen-free atmosphere to avoid surface oxidations. Examples of mouldings are pellets, spheres or granules having diameters of 3-7 mm. Furthermore, pelletted mouldings can be provided with a hole core to increase the external surface. Macroscopically, mouldings of this type have a smooth surface.

The catalysts which are to be used according to the invention, in the form of mouldings, must be prepared in a manner known to a person skilled in the art so that the resulting mouldings have compressive strengths of above 50 N, preferably compressive strengths of 100-400 N, on the moulding surface. This is of importance since lower compressive strengths cause decomposition or erosion of the mouldings by abrasion which would bring about a harmful contamination of the reaction product with metal powder. Moreover, the catalyst mouldings which are to be used according to the invention have specific internal surfaces of 10-90 $m^2/g$ in magnitude. Mouldings which have been prepared are tested for internal surfaces of this magnitude and accordingly for utility in the process according to the invention by methods which have been described by F. M. Nelsen and F. T. Eggertsen, Analyt. Chem. 30 (1958), 1387 and by S. J. Gregg and S. W. Sing, Adsorption, Surface Area and Porosity, London 1967, Chapters 2 and 8.

The hydrogenation is carried out at temperatures of 60°-125° C., preferably 70°-115° C. Lower temperatures would give high residence times or not achieve a substantially quantitative conversion of the sugar. Higher temperatures lead to uncontrollable side reactions such as caramelization, ether splitting or destructive hydrogenation, these possibly resulting in discolorations and the formation of harmful by-products.

The hourly space velocity is 25-100 g of the sugars designated as starting compounds per liter of catalyst. Adherence to the abovementioned reaction conditions gives unexpectedly high catalyst service lives of 16,000 hours and above, specific catalyst consumptions of at most 0.1% or below being achieved. The industrial advantages of the process according to the invention are not only the high yields resulting from virtually quantitative conversion, and the environmental advantages which result from the purity of the prepared product, but also the economical continuous mode of operation and the extremely low catalyst consumption.

After decompression, in which the excess hydrogen can be collected, and after it has been compressed and complemented with further hydrogen can be re-used, the aqueous solution of the sugar alcohol leaving the reactor can already be directly employed as a sugar replacement in liquid form.

However, it is also possible to remove the water from this solution in various ways, for example in a spray drier, by rotary drying or freeze drying. It has proved advantageous to concentrate the colourless and glass-clear solution of the sugar alcohol which has been obtained, in a falling film vaporizer or a similarly functioning apparatus, to a sugar alcohol content of about 70-80% by weight and then after further evaporation in a vacuum crystallization apparatus, to bring about partial or complete crystallization with cooling. The crystallized material can be brought to a uniform particle size by a subsequent grinding process and optionally by sieving. The resulting product is free-flowing.

Xylitol has a melting point of 93°-94° C. In the case of sorbitol, depending on the crystallization conditions, various crystalline modifications are prepared of which the γ-form having a melting point of 101° C. is the most stable.

Depending on the crystallization conditions, lactitol can be prepared either as the dihydrate having a melting point of 76°-78° C. or as the monohydrate having a melting point of 121°-123°. The solubility of the two hydrates in water is different; the monohydrate is less soluble than the dihydrate. The hydrates are non-hygroscopic and therefore have technological advantages in comparison with other polyols. Anhydrous lactitol can be obtained in crystalline form from solutions in absolute ethanol. It has a melting point of 146° C. and is hygroscopic.

Anhydrous maltitol can be isolated as an amorphous powder from solutions in absolute ethanol. Its melting point is 146°-148° C. and it is hygroscopic (Helv. Chim. Acta 20, (1937), 86-90).

All of the sugar alcohols prepared according to the invention have a content of catalyst components of below 1 ppm.

EXAMPLE 1

A vertically standing, heat-insulated high pressure tube of stainless steel 45 mm in internal diameter and 1 m in length was filled with 1.4 l of a hydrogenation catalyst which had been prepared by pelletting nickel powder, the pellets having a cylinder height of 5 mm and a diameter of 5 mm, a compressive strength of 147 N on the external surface of the cylinder and an internal surface of 33 $m^2/g$. Through this tube were continuously pumped, in particular in an upward direction, 250 ml/hour of a 40% strength solution of D-xylose in de-ionized oxygen-free drinking water having a pH of 7.0, together with a three-fold molar amount of highly pure hydrogen at a pressure of 300 bar.

The aqueous solution and the hydrogen had previously been jointly passed through a heat exchanger and heated to a temperature suitable for ensuring that the components entered the high pressure tube at a temperature of 95° C. The mixture of aqueous solution and excess hydrogen leaving the high pressure tube was passed through a cooler into a separator from where the hydrogen, after replacement of the amount consumed, was again pumped, together with fresh D-xylose solution, into the preheater and from there again into the high pressure tube.

The colourless, clear aqueous solution was depressurized and concentrated in a falling film vaporizer to a sugar alcohol content of about 70% and then, after further evaporation, crystallized in a vacuum crystallizer with cooling. This gave a white, slightly hygroscopic, odourless solid which was ground to give a finely crystalline powder. The resulting xylitol was otherwise highly pure and, in the stable rhombic crystalline form, had a melting point of 93°-94° C. The content of unhydrogenated D-xylose was ≦0.1%. The Ni content was <1 ppm. The efficiency of the catalyst was unchanged even after a running time of 5600 hours.

EXAMPLE 2

A high pressure tube similar to that of Example 1 was used to hydrogenate, at a temperature of 105° C. and a hydrogen pressure of 150 bar, an equal amount per hour of a 40% strength aqueous solution of D-xylose having a pH of 6.5, the hydrogen being brought together with the upward moving solution of D-xylose in the opposite flow direction to that in Example 1. The catalyst had been prepared by pelletting nickel powder. The pellets had a cylinder height of 5 mm and a diameter of 5 mm, a compressive strength of 149 N on the external surface of the cylinders and an internal surface of 62 m$^2$/g.

After a running time of 2800 hours with undiminished efficiency, the conversion of D-xylose was $\geq$99.9%. The content of unhydrogenated D-xylose in the crystallized xylitol, which had a purity of >99.5%, was $\leq$0.1%. The Ni content was <1 ppm.

EXAMPLE 3

A high pressure tube similar to that of Example 1 was used to hydrogenate, at a temperature of 115° C. and a hydrogen pressure of 300 bar, in the same manner as in Example 1, an equal amount per hour of a 40% strength aqueous solution of D-xylose having a pH of 7.5. The catalyst had been obtained by pelletting a pulverized nickel-iron alloy. The alloy contained a proportion of iron in nickel of 15%. The pellets had a cylinder height of 5 mm and a diameter of 5 mm, a compressive strength of 137 N on the external surface of the cylinder and an internal surface of 83 m$^2$/g. The crystalline xylitol obtained in a vacuum crystallizer by seeding with seed crystals had a purity of $\geq$99.5%. The content of unconverted D-xylose was 0.1%. The Ni and Fe contents together were <1 ppm. The efficiency of the catalyst was unchanged after a running time of 5400 hours.

EXAMPLE 4

A high pressure tube similar to that of Example 1 was used to hydrogenate, at a temperature of 110° C. and a hydrogen pressure of 300 bar, in the same manner as in Example 1, 150 ml per hour of a 40% strength aqueous solution of D-xylose having a pH of 6.5. The catalyst had been obtained by pelletting cobalt powder. The pellets had a cylinder height of 5 mm and a diameter of 5 mm, a compressive strength of 225 N on the external surface of the cylinder and an internal surface of 19 m$^2$/g. The xylitol obtained in a vacuum rotary drier had a content of unconverted D-xylose of $\leq$0.2%. The cobalt content was <1 ppm. The efficiency of the catalyst was unchanged even after a running time of 1000 hours.

EXAMPLE 5 (Comparative Example)

A high pressure tube similar to that of Example 1 was used to hydrogenate, at a temperature of 110° C. and a hydrogen pressure of 300 bar, in the same manner as in Example 1 an equal amount per unit time of a 40% strength aqueous solution of D-xylose having a pH of 6.5. The catalyst had been prepared by treating an inert spherical Al$_2$O$_3$ carrier (sphere diameter: 5 mm) with an aqueous nickel salt solution followed by conversion of the nickel to the metallic state by reduction in a current of hydrogen. The nickel content of the catalyst was 20%. The internal surface of the catalyst was 140 m$^2$/g. The xylitol obtained in a vacuum crystallizer had a purity of 96.8%. The content of unconverted D-xylose was 1.5%. In addition, other extraneous sugar components were detected in an amount of 1.7%, and therefore it was impossible to use the xylitol obtained in this manner in the form in which it was prepared as a sugar replacement without environmentally expensive purification procedures. Although increasing the reaction temperature from 110° to 125° C. allowed the proportion of unconverted D-xylose to be reduced to a value of 1.2%, the proportion of impurities of an organic nature simultaneously increased to a value of 3.2%, these including lyxitol and arabinitol in an amount of about 1.4%. Moreover, the reaction product was contaminated with 36 ppm of Ni.

EXAMPLE 6 (Comparative Example)

A high pressure tube similar to that of Example 1 was used to hydrogenate, at a temperature of 115° C. and a hydrogen pressure of 300 bar, in the same manner as in Example 1, the same amount per hour of a 40% strength aqueous solution of D-xylose having a pH of 6.5. The catalyst had been prepared by treating an inert, spherical Al$_2$O$_3$ carrier (sphere diameter: 5 mm) w aqueous nickel salt and iron salt solutions followed by conversion of the nickel and iron to the metallic state by reduction in a current of hydrogen. The nickel content of the catalyst was 16%, and the iron content 4%. The internal surface of the catalyst was 155 m$^2$/g.

The xylitol obtained by evaporation in a vacuum crystallizer had a purity of 94.6%. The content of unconverted D-xylose was 1.4%. In addition, organic impurities were detected in an amount of 4.0% and also Ni impurities of 32 ppm and Fe impurities of 11 ppm, and therefore it was impossible to use the resulting sugar alcohol as a sugar replacement without environmentally costly purification measures. A significant decline in catalyst activity was observed after a running time of only 750 hours.

EXAMPLE 7

A high pressure tube similar to that of Example 1 was filled with 1.4 l of a hydrogenation catalyst which had been prepared by pelletting nickel powder, the pellets having a cylinder height of 5 mm and a diameter of 5 mm, a compressive strength of 147 N on the external surface of the cylinder and an internal surface of 33 m$^2$/g. Through this tube were continuously pumped, in particular in an upward direction, 250 ml/hour of a 40% strength solution of $\alpha$-D-glucose in deionized oxygen-free drinking water having a pH of 7.0, together with a threefold fold molar amount of highly pure hydrogen at a pressure of 300 bar.

The aqueous solution and the hydrogen had previously been jointly passed through a heat exchanger and heated to a temperature suitable for ensuring that the components entered the high pressure tube at a temperature of 95° C. The mixture of aqueous solution and excess hydrogen leaving the high pressure tube was passed through a cooler into a separator from where the hydrogen, after replacement of the amount consumed, was again pumped, together with fresh $\alpha$-D-glucose solution, into the preheater and from there again into the high pressure tube.

The colourless, clear aqueous solution was depressurized and concentrated in a falling film vaporizer to a sugar alcohol content of about 70% and then, after further evaporation, crystallized in a vacuum crystallizer with cooling. This gave a white, slightly hygroscopic, odourless solid which was ground to give a finely crystalline powder. The resulting sorbitol (D-glucitol) was otherwise highly pure and, in the stable $\gamma$-form, had a melting point of 101° C. The content of unhydrogenated $\alpha$-D-glucose was $\leq$0.1%. The Ni content was <1 ppm. The efficiency of the catalyst was unchanged even after a running time of 9800 hours.

EXAMPLE 8

A high pressure tube similar to that of Example 1 was used to hydrogenate, at a temperature of 105° C. and a hydrogen pressure of 150 bar, an equal amount per hour to that of Example 1 of a 40% strength aqueous solution of α-D-glucose having a pH of 6.5, the hydrogen being brought together with the upward moving solution of α-D-glucose in the opposite flow direction to that described in Example 1. The catalyst had been prepared by pelletting nickel powder. The pellets had a cylinder height of 5 mm and a diameter of 5 mm, a compressive strength of 149 N on the external surface of the cylinders and an internal surface of 62 m²/g.

After a running time of 4200 hours, with undiminished efficiency, the conversion of α-D-glucose was ≧99.9%. The content of unhydrogenated α-β-D-glucose in the crystallized sorbitol (D-glucitol), which had a purity of ≧99.5%, was ≦0.1%. The Ni content was <1 ppm.

EXAMPLE 9

A high pressure tube similar to that of Example 1 was used to hydrogenate, at a temperature of 115° C. and a hydrogen pressure of 300 bar, in the same manner as in Example 1, an equal amount per hour of a 40% strength aqueous solution of α-D-glucose having a pH of 7.5. The catalyst had been obtained by pelletting a pulverulent nickel-iron alloy. The proportion of iron in nickel in this alloy was 15%. The pellets had a cylinder height of 5 mm and a diameter of 5 mm, a compressive strength of 137 N on the external surface of the cylinder and an internal surface of 83 m²/g. The crystalline sorbitol (D-glucitol) obtained in a vacuum crystallizer had a purity of ≧99.5%. The content of unconverted α-D-glucose was 0.1%. The Ni and Fe contents together were <1 ppm. The efficiency of the catalyst was still unchanged after a running time of 8400 hours.

EXAMPLE 10

A high pressure tube similar to that of Example 1 was used to hydrogenate, at a temperature of 110° C. and a hydrogen pressure of 300 bar, in the same manner as in Example 1, 150 ml of a 35% strength aqueous solution of α-D-glucose having a pH of 6.5. The catalyst had been obtained by pelletting cobalt powder. The pellets had a cylinder height of 5 mm and a diameter of 5 mm, a compressive strength of 225 N on the external surface of the cylinder and an internal surface of 19 m²/g. The sorbitol (D-glucitol) obtained in a vacuum rotary evaporator had a content of unconverted α-D-glucose of ≦0.2%. The cobalt content was <1 ppm. The efficiency of the catalyst was unchanged even after a running period of 1000 hours. Example 11 (Comparative Example)

A high pressure tube similar to that of Example 1 was used to hydrogenate, at a temperature of 110° C. and a hydrogen pressure of 300 bar, in the same manner as in Example 1, an equal amount per unit time of a 40% strength aqueous solution of α-D-glucose having a pH of 6.5. The catalyst had been prepared by treating an inert spherical Al₂O₃ carrier (sphere diameter: 5 mm) with an aqueous nickel salt solution followed by conversion of the nickel into the metallic state by reduction in a current of hydrogen. The nickel content of the catalyst was 20%. The internal surface of the catalyst was 140 m²/g. The sorbitol (D-glucitol) obtained in a vacuum crystallizer had a purity of 94.9%. The content of unconverted α-D-glucose was 1.9%. In addition, other extraneous sugar components were detected in an amount of 3.2% (including mannitol in an amount of 2.1%) and therefore that it was impossible to use the sorbitol obtained in this manner in the form in which it was prepared as a sugar replacement without environmentally expensive purification procedures. Although increasing the reaction temperature from 110° to 125° C. allowed the proportion of unconverted α-D-glucose to be reduced to a value of 0.6%, the proportion of impurities of an organic nature simultaneously increased to a value of 6.2% (including mannitol in an amount of 3.9%). Moreover, the reaction product was contaminated with 42 ppm of Ni.

EXAMPLE 12 (Comparative Example)

A high pressure tube similar to that of Example 1 was used to hydrogenate, at a temperature of 115° C. and a hydrogen pressure of 300 bar, in the same manner as in Example 1, an equal amount per hour of a 40% strength aqueous solution of α-D-glucose having a pH value of 6.5. The catalyst had been prepared by treating an inert, spherical Al₂O₃ carrier (sphere diameter: 5 mm) with aqueous nickel salt and iron salt solutions, followed by conversion of the nickel and iron to the metallic state by reduction in a current of hydrogen. The nickel content of the catalyst was 16%, and the iron content 4%. The internal surface of the catalyst was 155 m²/g. The sorbitol (D-glucitol) obtained by evaporation in a vacuum crystallizer had a purity of 93.8%. The content of unconverted α-D-glucose was 1.6%. In addition, organic impurities were detected in an amount of 4.6% (including mannitol in an amount of 2.9%), and also Ni impurities of 38 ppm and Fe impurities of 16 ppm, and therefore it was impossible to use the resulting sugar alcohol as a sugar replacement without environmentally expensive purification measures. A significant decline in the catalyst activity was observed after a running time of only 800 hours.

EXAMPLE 13

A high pressure tube similar to that of Example 1 was filled with 1.4 l of a hydrogenation catalyst which had been prepared by pelletting nickel powder, the pellets having a cylinder height of 5 mm and a diameter of 5 mm, a compressive strength of 147 N on the external surface of the cylinder and an internal surface of 33 m²/g. Through this tube were continuously pumped, in particular in an upward direction 250 ml/hour of a 40% strength solution of 4-O-β-D-galactopyranosyl-α-D-glucopyranose in deionized oxygen-free drinking water having a pH of 7.0, together with a three-fold molar amount of highly pure hydrogen at a pressure of 300 bar.

The aqueous solution and the hydrogen had previously been jointly passed through a heat exchanger and heated to a temperature suitable for ensuring that the components entered the high pressure tube at a temperature of 90° C. The mixture of aqueous solution and excess hydrogen leaving the high pressure tube was passed through a cooler into a separator from where the hydrogen, after replacement of the amount consumed, was again pumped, together with fresh 4-O-β-D-galactopyranosyl-α- D-glucopyranose, into the preheater and from there again into the high pressure tube.

The colourless, clear aqueous solution was depressurized and concentrated in a falling film vaporizer to a sugar alcohol content of about 80% and then, after further evaporation, crystallized in a vacuum crystallizer with cooling. Depending on the crystallization conditions and the residual water content of the concentrated solution, this procedure gave either the dihydrate having a melting point of 76°–78° C. or the monohydrate having a melting point of 121°–123° C. The resulting 4-O-β-D-galactopyranosyl-D-glucitol was otherwise highly pure (purity ≧99.6%). The content of unhydrogenated 4-O-β-D-galactopyranosyl-α-D-glucopyranose was ≦0.1%. The content of sorbitol and dulcitol was ≦0.1%. It was not possible to detect 4-O-β-D-galactopyranosyl-D-mannitol or mannitol. The Ni content was <1 ppm. The efficiency of the catalyst was unchanged even after a running time of 8700 hours.

EXAMPLE 14

A high pressure tube similar to that of Example 1 was used to hydrogenate, at a temperature of 105° C. and a hydrogen pressure of 150 bar, an equal amount per hour to that of Example 1 of a 40% strength aqueous solution of 4-O-β-D-galactopyranose-α-D-glucopyranose having a pH of 6.5, the hydrogen being brought together with the upward moving solution of 4-O-β-D-galactopyranosyl-α-D-glucopyranose in the opposite flow direction to that described in Example 1. The catalyst had been prepared by pelletting nickel powder. The pellets had a cylinder height of 5 mm and a diameter of 5 mm, a compressive strength of 149 N on the external surface of the cylinder and an internal surface of 62 $m^2/g$.

After a running time of 2500 hours with undiminished efficiency, the content of 4-O-β-D-galactopyranosyl-D-glucitol of the reaction mixture which had been evaporated to dryness in a rotary evaporator was 99.4%. The content of unhydrogenated 4O-β-D-galactopyranosyl-α-D-glucopyranose was ≦0.1%. The content of sorbitol and dulcitol was 0.1%. It was impossible to detect 4-O-β-D-galactopyranosyl-D-mannitol or mannitol. The Ni content was <1 ppm.

EXAMPLE 15

A high pressure tube similar to that of Example 1 was used to hydrogenate, at a temperature of 115° C. and a hydrogen pressure of 300 bar, in the same manner as in Example 1, an equal amount per hour of a 40% strength aqueous solution of 4-O-β-D-galactopyranosyl-α-D-glucopyranose having a pH of 7.5. The catalyst was prepared by pelletting a pulverulent nickel-iron alloy. The alloy contained a proportion of iron in nickel of 15%. The pellets had a cylinder height of 5 mm and a diameter of 5 mm, a compressive strength of 137 N on the external surface of the cylinder and an internal surface of 83 $m^2/g$. The 4-O-β-D-galactopyranosyl-α-D-glucitol obtained in a vacuum crystallizer had a purity of 99.3%. The content of unconverted 4-O-β-D-galactopyranosyl-α-D-glucose was 0.1%. The sorbitol and dulcitol content was 0.1%. It was impossible to detect 4-O-β-D-galactopyranosyl-D-mannitol or mannitol. The Ni and Fe contents were <1 ppm. The efficiency of the catalyst was unchanged after a running time of 8000 hours.

EXAMPLE 16

A high pressure tube similar to that of Example 1 was used to hydrogenate, at a temperature of 110° C. and a hydrogen pressure of 200 bar, in the same manner as in Example 1, an equal amount of a 30% strength aqueous solution of 4-O-β-D-galactopyranosyl-α-D-glucopyranose having a pH of 6.5. The catalyst was obtained by pelletting a pulverulent nickel-cobalt alloy. The proportion of cobalt in nickel in this alloy was 10%. The pellets had a cylinder height of 5 mm and a diameter of 5 mm, a compressive strength of 147 N on the external surface of the cylinder and an internal surface of 29 $m^2/g$. The 4-O-β-D-galactopyranosyl-α-D-glucitol obtained in a vacuum rotary evaporator had a purity of 99.1%. The content of unconverted 4-O-β-D-galactopyranosyl-α-D-glucopyranose was 0.2%. The sorbitol content was 0.2%. The proportion of dulcitol was 0.15%. It was impossible to detect 4-O-β-D-galactopyranosyl-D-mannitol. The Ni and Co contents were <1 ppm. The efficiency of the catalyst was unchanged even after a running time of 1000 hours.

EXAMPLE 17 (Comparative Example)

A high pressure tube similar to that of Example 1 was used to hydrogenate, at a temperature of 100° C. and a hydrogen pressure of 300 bar, in the same manner as in Example 1, an equal amount per unit time, of a 40% strength aqueous solution of 4-O-β-D-galactopyranosyl-α-D-glucopyranose having a pH of 7.0. The catalyst had been prepared by treating an inert spherical $Al_2O_3$ carrier (sphere diameter: 5 mm) with an aqueous nickel salt solution followed by conversion of the nickel to the metallic state by reduction in a current of hydrogen. The nickel content of the catalyst was 20%. The internal surface of the catalyst was 145 $m^2/g$. The 4-O-β-D-galactopyranosyl-α-D-glucitol obtained in a vacuum crystallizer had a purity of 93.9%. The content of unconverted 4-O-β-D-galactopyranosyl-α-D-glucopyranose was 1.9%. The sorbitol and dulcitol contents were 0.4 and 0.2% respectively. In addition, other impurities were detected in an amount of 3.6%, including 4-O-β-D-galactopyranosyl-D-mannitol in an amount of 2.6%, and therefore it was impossible to use the 4-O-β-D-galactopyranosyl-α-D-glucitol which had been obtained in this manner in the form in which it was prepared as a sugar replacement without environmentally expensive purification procedures. Moreover, a decline in the catalyst activity was observed after a running time of only 800 hours. Although increasing the reaction temperature from 100° to 120° C. allowed the proportion of unconverted 4-O-β-D-galactopyranosyl-α-D-glucopyranose to be reduced to a value of 0.6%, the proportion of impurities simultaneously increased to a value of 6.4%. This included 4-O-β-D-galactopyranosyl-D-mannitol in an amount of 3.2%. Moreover, the reaction product was contaminated with 42 ppm of Ni.

EXAMPLE 18 (Comparative Example)

A high pressure tube similar to that of Example 1 was used to hydrogenate, at a temperature of 100° C. and a hydrogen pressure of 300 bar, in the same manner as in Example 1, an equal amount per hour of a 40% strength aqueous solution of 4-O-β-D-galactopyranosyl-α-D-glucopyranose having a pH of 6.5. The catalyst had been prepared by treating an inert, spherical $Al_2O_3$ carrier (sphere diameter: 5 mm) with aqueous nickel salt and iron salt solutions followed by conversion of the nickel and iron to the metallic state by reduct in a current of hydrogen. The nickel content of the catalyst was 16%, and the iron content 4%. The internal surface of the catalyst was 151 $m^2/g$. The 4-O-β-D-galactopyranosyl-α-D-glucitol obtained by evaporation in a vacuum crystallizer had a purity of 91.2%. The content of unconverted 4-O-β-D-galactopyranosyl-α-D-glucopyranose was 1.6%. The sorbitol and dulcitol contents were 0.3 and 0.1% respectively. In addition, other organic impurities were detected in an amount of 6.8%, including 4-O-β-D-galactopyranosyl-D-mannitol in an amount of 2.9%, and also Ni impurities of 36 ppm and Fe impurities of 14 ppm, and therefore it was impossible to use the resulting sugar alcohol as a sugar replacement without environmentally expensive purification measures.

EXAMPLE 19

A high pressure tube similar to that of Example 1 was filled with 1.4 l of a hydrogenation catalyst which had been prepared by pelletting nickel powder, the pellets having a cylinder height of 5 mm and a diameter of 5 mm, a compressive strength of 174 N on the external surface of the cylinder and an internal surface of 33 m$^2$/g. Through this tube were continuously pumped, in particular in an upward direction, 250 ml/hour of a 40% strength solution of 4-O-β-D-glucopyranosyl-α-D-glucopyranose in deionized oxygen-free drinking water having a pH of 7.0, together with a five-fold molar amount of highly pure hydrogen at a pressure of 300 bar.

The aqueous solution and the hydrogen had previously been jointly passed through a heat exchanger and heated to a temperature suitable for ensuring that the components entered the high pressure tube at a temperature of 80° C. The mixture of aqueous solution and excess hydrogen leaving the high pressure tube was passed through a cooler into a separator from where the hydrogen, after replacement of the amount consumed, was again pumped, together with fresh 4-O-α-D-glucopyranosyl-α-D-glucopyranose, into the preheater and from there again into the high pressure tube.

The colourless, clear aqueous solution was depressurized and concentrated in a falling film vaporizer to a sugar alcohol content of about 80% and then, after further evaporation, crystallized in a vacuum crystallizer with cooling and optionally with the addition of seed crystals. The crystalline 4-O-α-D-glucopyranosyl-D-sorbitol had a purity of ≦99.6%. The content of unhydrogenated 4-O-α-D-glucopyranosyl-α-D-glucopyranose was ≦0.1%. The sorbitol content was ≦0.3%. Mannitol was undetectable. The Ni content was <1 ppm. The efficiency of the catalyst was unchanged even after a running time of 6200 hours.

EXAMPLE 20

A high pressure tube similar to that of Example 1 was used to hydrogenate, at a temperature of 85° C. and a hydrogen pressure of 150 bar, an equal amount per hour to that of Example 1 of a 40% strength aqueous solution of 4-O-α-D-glucopyranose-α-D-glucopyranose having a pH of 6.5, the hydrogen being brought together with the upward moving solution of 4-O-α-D-glucopyranosyl-α-D-glucopyranose in the opposite flow direction to that described in Example 1. The catalyst was prepared by pelletting nickel powder. The pellets had a cylinder height of 5 mm and a diameter of 5 mm, a compressive strength of 149 N on the external surface of the cylinder and an internal surface of 62 m$^2$/g.

After a running time of 2500 hours with undiminished efficiency, the content of 4-O-α-D-glucopyranosyl-D-sorbitol in the reaction mixture which had been evaporated to dryness in a rotary evaporator was 99.4%. The content of unhydrogenated 4-O-α-D-glucopyranosyl-α-D-glucopyranose was <0.1%. The sorbitol content was 0.3%. The Ni content was <1 ppm.

EXAMPLE 21

A high pressure tube similar to that of Example 1 was used to hydrogenate, at a temperature of 80° C. and a hydrogen pressure of 300 bar, in the same manner as in Example 1, an equal amount per hour of a 40% strength aqueous solution of 4-O-α-D-glucopyranosyl-α-D-glucopyranose having a pH of 7.5. The catalyst was obtained by pelletting a pulverulent nickel-iron alloy. The alloy contained a proportion of iron in nickel of 15%. The pellets had a cylinder height of 5 mm and a diameter of 5 mm, a compressive strength of 137 N on the outer surface of the cylinder and an internal surface of 83 m$^2$/g. The 4-O-α-D-glucopyranosyl-α-D-sorbitol obtained in a vacuum evaporator had a purity of 99.3%. The content of unconverted 4-O-α-D-glucopyranosyl-α-D-glucose was 0.1%. The sorbitol content was 0.3%. The Ni and Fe contents were <1 ppm. The efficiency of the catalyst was unchanged even after a running time of 4200 hours.

EXAMPLE 22

A high pressure tube similar to that of Example 1 was used to hydrogenate, at a temperature of 100° C. and a hydrogen pressure of 200 bar, in the same manner as in Example 1, an equal amount of a 30% strength aqueous solution of 4-O-α-D-glucopyranosyl-α-D-glucopyranose having a pH of 6.5. The catalyst was obtained by pelletting cobalt powder. The pellets had a cylinder height of 5 mm and a diameter of 5 mm, a compressive strength of 225 N on the outer surface of the cylinder and an internal surface of 19 m$^2$/g. The 4-O-α-D-glucopyranosyl-α-D-sorbitol obtained in a vacuum rotary drier had a purity of 99.1%. The content of unconverted 4-O-α-D-glucopyranosyl-α-D-glucopyranose was 0.1%. The sorbitol content was 0.2%. The Co content was <1 ppm. The efficiency of the catalyst was unchanged even after a running time of 1000 hours.

EXAMPLE 23 (Comparative Example)

A high pressure tube similar to that of Example 1 was used to hydrogenate, at a temperature of 100° C. and a hydrogen pressure of 300 bar, in the same manner as in Example 1, an equal amount per unit time of a 40% strength aqueous solution of 4-O-α-D-glucopyranosyl-α-D-glucopyranose having a pH of 7.0. The catalyst had been prepared by treating an inert spherical Al$_2$O$_3$ carrier (sphere diameter: 5 mm) with an aqueous nickel salt solution followed by conversion of the nickel into the metallic state by reduction in a current of hydrogen. The nickel content of the catalyst was 20%. The internal surface of the catalyst was 148 m$^2$/g. The 4-O-α-D-glucopyranosyl-α-D-sorbitol obtained in a vacuum evaporator had a purity of 92.9%. The content of unconverted 4-O-α-D-glucopyranosyl-α-D-glucopyranose was 1.4%. The sorbitol content was 3.6%. In addition, unknown impurities were detected in an amount of 2.1%, and therefore it was impossible to use the 4-O-α-D-glucopyranosyl-α-D-sorbitol which had been obtained in this manner in the form in which it had been prepared as a sugar replacement without environmentally expensive purification procedures. Moreover, a decline in catalyst activity was observed after a running time of only 700 hours. Although increasing the reaction temperature from 100° to 120° C. allowed the proportion of unconverted 4-O-α-D-glucopyranosyl-α-D-glucopyranose to be reduced to a value of 0.2%, the proportion of sorbitol simultaneously increased to a value of 4.2%. Moreover, the reaction product was contaminated with 48 ppm of Ni.

EXAMPLE 24 (Comparative Example)

A high pressure tube similar to that of Example 1 was used to hydrogenate, at a temperature of 100° C. and a hydrogen pressure of 300 bar, in the same manner as in Example 1, an equal amount per hour of a 40% strength aqueous solution of 4-O-α-D-glucopyranosyl-α-D-glucopyranose having a pH of 6.5. The catalyst had been prepared by treating an inert, spherical Al$_2$O$_3$ carrier (sphere diameter: 5 mm) with aqueous nickel salt and iron salt solutions followed by conversion of the nickel and iron to the metallic state by reduction in a current of hydrogen. The nickel content of the catalyst was 16%, and the iron content 4%. The internal surface of the catalyst was 151 m$^2$/g. The 4-O-α-D-glucopyranosyl-α-D-sorbitol obtained by evaporation in a rotary evaporator had a purity of 93.4%. The content of unconverted 4-O-α-D-glucopyranosyl-α-D-glucopyranose was 1.0%. The sorbitol content was 4.3%. In addition, unknown organic impurities were detected in an amount of 1.3% and also Ni impurities of 31 ppm and Fe impurities of 12 ppm and therefore it was impossible to use the resulting sugar alcohol as a sugar replacement without environmentally expensive purification measures.

What is claimed is:

1. A process for the preparation of an epimer-free sugar alcohol, having a remaining catalyst residue of below 1 ppm, from the group consisting of xylitol, sorbitol (D-glucitol), 4-O-β-D-galactopyranosyl-D-glucitol and 4-Oα-D-glucopyranosyl-D-sorbitol by catalytic hydrogenation of the corresponding sugar D-xylose, α-D-glucose, 4-O-β-D-galactopyranosyl-α-D-glucopyranose or 4-O-α-D-glucopyranosyl-α-D-glucopyranose, respectively, in aqueous solution using hydrogen under elevated pressure and at elevated temperature, wherein the hydrogenation is carried out continuously at a hydrogen pressure of 150 to 500 bar and temperature of 60° to 125° C. in a reaction zone, by a fixed bed process over hydrogenation catalysts in the form of carrier-free mouldings having a compressive strength of more than 50 N onto the surface of the mouldings, and an internal surface of 10 to 90 m$^2$/g, said mouldings being made from one or more elements of the iron group of the periodic table, wherein the reaction is carried out at an hourly space velocity of 25 to 100 g of the sugar or the starting compound per liter of catalyst.

2. The process of claim 1, wherein the mouldings are of the type prepared from pressed metal powders composed of nickel, cobalt or mixtures thereof or alloys with one another or with iron, having a macroscopically smooth surface.

3. The process of claim 2, wherein the catalyst mouldings are composed of nickel or mixtures containing at lest 70% nickel.

4. The process of claim 1, wherein the hydrogenation catalyst are cylindrical or spherical mouldings having a diameter of 3-7 mm.

5. The process of claim 1, wherein the hydrogenation of the sugars is carried out in 15 to 45% strength aqueous solution at a pH of 3.5 to 10.5.

6. The process of claim 5, wherein the aqueous solution is of 35 to 40% strength by weight.

7. The process of claim 5, wherein the aqueous solution of D-xylose or α-D-glucose has a pH value of 3.5 to 8.

8. The process of claim 5, wherein the aqueous solution of lactose or maltose has a pH value of 5.5 to 10.5.

9. The process of claim 5, wherein the aqueous solution has a pH value of 6 to 7.5.

10. The process of claim 1, wherein the catalyst mouldings have a compressive strength of 100 to 400 N.

11. The process of claim 1, which is carried out at a hydrogen pressure of 150 to 300 bar.

12. The process of claim 1, wherein the carrier-free catalyst moulding are prepared from metal powders with the addition of graphite and/or adhesives in an amount of 0.5 to 3% by weight, relative to the total weight of the components forming the catalyst.

13. The process of claim 1, which is carried out at a temperature of 70° to 115° C.

* * * * *